US008613384B2

(12) United States Patent
Pastorelli et al.

(10) Patent No.: US 8,613,384 B2
(45) Date of Patent: Dec. 24, 2013

(54) SURGICAL STAPLING INSTRUMENT AND A STAPLE CARTRIDGE AND STAPLE FOR SUCH AN INSTRUMENT

(75) Inventors: Alessandro Pastorelli, Rome (IT); Federico Bilotti, Latina (IT); William Bruce Weisenburgh, II, Maineville, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1112 days.

(21) Appl. No.: 12/307,752

(22) PCT Filed: May 21, 2007

(86) PCT No.: PCT/EP2007/004489
§ 371 (c)(1),
(2), (4) Date: Sep. 29, 2009

(87) PCT Pub. No.: WO2008/003371
PCT Pub. Date: Jan. 10, 2008

(65) Prior Publication Data
US 2012/0325893 A1  Dec. 27, 2012

(30) Foreign Application Priority Data
Jul. 7, 2006 (EP) .................................. 06116854

(51) Int. Cl.
*A61B 17/068* (2006.01)
(52) U.S. Cl.
USPC .................................... 227/177.1; 227/179.1
(58) Field of Classification Search
USPC ............... 227/19, 176.1, 177.1, 178.1, 180.1, 227/181.1; 606/153, 219
See application file for complete search history.

(56) References Cited

U.S. PATENT DOCUMENTS

| 2,142,782 | A | * | 1/1939 | Gillette | 411/474 |
| 3,771,526 | A | * | 11/1973 | Rudie | 606/153 |
| 7,547,312 | B2 | | 6/2009 | Bauman et al. | |
| 2004/0004105 | A1 | * | 1/2004 | Jankowski | 227/176.1 |
| 2006/0180633 | A1 | * | 8/2006 | Emmons | 227/176.1 |

FOREIGN PATENT DOCUMENTS

| EP | 0509513 B1 | 7/1996 |
| EP | 1016378 A1 | 7/2000 |
| JP | 58188442 A | 11/1983 |
| WO | WO 01/54594 A1 | 8/2001 |
| WO | WO 0154594 A1 * | 8/2001 |
| WO | WO 2004/105621 A1 | 12/2004 |

OTHER PUBLICATIONS

European Search Report dated Nov. 13, 2006, for European Application No. 06116854.8.
International Search Report dated Sep. 13, 2007, for International Application No. PCT/EP2007/004489.

* cited by examiner

*Primary Examiner* — Alexandra Elve
*Assistant Examiner* — Nathaniel Chukwurah (57) ABSTRACT

A surgical stapling instrument comprises a cartridge device with a row of staples and a wavy first tissue interface, and an anvil having a wavy second tissue interface which cooperates with the first tissue interface for clamping tissue therebetween and forming the staples exiting from the cartridge device, a staple driving device adapted to drive the staples out of the cartridge device towards the anvil, wherein the staples are non-symmetrical U-shaped with two legs protruding toward the anvil and a transverse basis connecting the legs, wherein the basis is inclined with respect to the longitudinal direction of the legs and has a length greater than the staple projection on a plane perpendicular to the longitudinal direction of the legs.

7 Claims, 11 Drawing Sheets

SURGICAL STAPLING INSTRUMENT AND A STAPLE CARTRIDGE AND STAPLE FOR SUCH AN INSTRUMENT

The invention relates to a surgical stapling instrument, which can be used for applying surgical staples to tissue and in particular for performing an anastomosis. The invention relates also to a cartridge device for such a surgical stapling instrument and to a surgical staple.

Generally, in the performance of a surgical anastomotic stapling operation, two pieces of lumen or tubular tissue, e. g., intestinal tissue, are attached together by a closed row of staples. In performing the anastomosis with a surgical stapling instrument, the two pieces of tubular tissue are clamped together between an anvil provided with an array of staple forming grooves and a staple holder or cartridge device provided with a plurality of staple receiving slots arranged in a closed row or array in which the staples are received. A staple pusher is advanced to drive the staples into the tissue and form the staples against the anvil. Moreover, an annular knife or cutting edge is advanced to cut the excess tissue clamped between the anvil and the staple holder.

As a result, the donut-shaped section of tissue is severed from each lumen and remains on the anvil shaft. The tubular tissue joined by the closed row of staples is unclamped by moving the anvil relative to the staple holder, usually by advancing the anvil shaft distally to move the anvil away from the staple holder. The stapling instrument is removed by pulling the anvil through the anastomotic orifice defined by the pieces of tubular tissue attached by the array of staples.

As the row of staples is concerned, it usually comprises a group of single metallic or synthetic staples arranged with or without overlap and each staple having a substantially symmetrical shape with two longitudinal legs connected by a transverse crown or basis perpendicular to the longitudinal direction of the legs. Traditionally, the opposite tissue interfaces (i.e. the surfaces which directly contact and clamp the tissue between them) of the anvil and the staple holder or cartridge device have a planar shape perpendicular to the direction of relative movement between the anvil and the cartridge device. This configuration leads to a stapled seam and, hence, to a circumference of the anastomotic lumen which is shorter than the outer circumference of the circular stapler. As a result, it is often difficult to retract the instrument from the site of the operation, because it is difficult to move the anvil through the opening constraint by the closed row of staples, which is somewhat stiff. Moreover, after the operation, the incidence of clinical stenosis at the site of the anastomosis is not rare.

In order to overcome this problem, a generally wavy shaped configuration of the tissue interfaces of the stapler has been proposed. Thanks to the wavy shape and to the resulting inclination of the tissue interfaces with respect to the clamping direction of the stapler, the total length of the tissue interfaces and the resulting stapled seam is greater than their linear extension. In other words, the total length of the tissue interfaces is greater than their projection on a plane perpendicular to the staple direction. In this way, for a given stapler dimension the length of the stapled seam and hence the circumference and diameter of the resulting anastomotic orifice can be increased. Examples of these known surgical stapling instruments have been disclosed in WO 01/54594 (for a circular stapler) and EP 1 254 636 A2 (for linear staplers).

Although the known surgical stapling instruments are very beneficial and greatly facilitate the performance of an anastomosis or other kinds of surgical stapling and resection, they still involve some problems. The stapled seam is relatively stiff and tends to maintain its wavy and sometimes shrinked shape so that flattening and widening of the stapled site results in undesired tissue tensioning. This tissue tensioning could lead to post-operative stricture and stenosis. A reduction of the incidence of these complications is desirable.

Moreover, with the wavy shape of the tissue interfaces and a wavy shape of the line defining the row of staples, generally the staples must be driven and formed at varying angles from the plane perpendicular to the stapling direction. This adds complexity to the staple driving device, and a simple axial drive mechanism, like in conventional stapling instruments, is generally not sufficient.

In view of the above mentioned drawbacks of the prior art, the object of the invention is to provide a surgical stapling instrument, e.g. for performing an anastomosis, in which said instrument is capable of creating stapled seams which are less stiff and generally longer than those obtainable by prior art techniques in order to obviate unwanted tissue tension and to reduce the risk of undesirable clinical complications during the healing process.

Within the general scope of the principle object it is a further object of the invention to provide a surgical stapling instrument having a generally wavy tissue interface, but a less complex staple drive mechanism than those known in the art.

A yet further object of the invention is to provide a staple cartridge device and a surgical staple for use in the surgical stapling instrument.

These and other objects are achieved by a surgical stapling instrument comprising a frame having a body portion and a handle, a staple fastening assembly in the distal region of said instrument, the staple fastening assembly including a cartridge device which comprises at least one row of staples and a generally wavy first tissue interface, and an anvil which is movable relative to the cartridge device and having a generally wavy second tissue interface adapted to cooperate with the first tissue interface of the cartridge device for clamping tissue therebetween and forming the ends of the staples exiting from the cartridge device, a moving device adapted to move the anvil relative to the cartridge device, a staple driving device adapted to drive the staples out of the cartridge device towards the anvil, wherein the staples comprise one or more substantially U-shaped staples having two legs with free pointed ends facing toward the anvil and a transverse basis (so called "crown") connecting the legs, wherein the basis is inclined with respect to the longitudinal direction of the legs, such that the basis has a length greater then its projection on a plane perpendicular to the longitudinal direction of the legs. This allows to adapt the local orientation of the stapled seam, which can be seen as a succession of overlapping staple "crowns", to the wavy orientation of the clamped tissue and, at the same time, to drive all staples in the same "firing"-direction of the stapling instrument, which is inclined to the orientation of the clamped tissue. As a result, it is possible to obtain a longer and less stiff stapled seam by means of a simplified staple drive mechanism. Advantageously, each staple is arranged in the cartridge device such that its basis extends substantially in a direction parallel to the direction of the corresponding portion of the first tissue interface through which the staple is expellable by the staple driving device and the legs of all staples extend in substantially the same staple driving direction, i.e. the "firing"-direction of the stapler.

In accordance with an embodiment of the invention, the staple driving device comprise pushers having a sloped push surface contacting directly the sloped basis of the staples, wherein the push surfaces are inclined with respect to a plane perpendicular to the staple driving direction and extend in a direction parallel to the direction of the corresponding portion of the first tissue interface. This allows to provide a very simple staple drive mechanism with a plurality of integrally connected pushers which can be advanced and retracted all together in the same direction.

In accordance with a preferred embodiment, the sloped basis of the staple is substantially straight and defines with the plane perpendicular to the longitudinal direction of the staple legs an angle comprised between 5° and 85°, preferably between 20° and 70° and even more preferably between 30° and 60°. A variety of staples having different staple basis inclinations can be provided in order to adapt the curve defined by the crowns of the staples arranged in the cartridge to the curve defined by the wavy tissue interfaces of the stapling instrument.

Preferably, the staple has a shape such as to extend completely within a single plane.

In accordance with an important aspect of the invention, the cartridge device defines a plurality of guide slots adapted to slidably house said staples and opening out in the first tissue interface, in which all guide slots are parallel to each other and extend in the same axial staple driving direction which corresponds to the "firing"-direction of the stapling instrument, leading to a noticeable simplification of the staple drive mechanism.

These and other features and advantages of the present invention shall be made apparent from the accompanying drawings and the description thereof, which illustrate embodiments of the invention and, together with the general description of the invention given above and the detailed description of the embodiments given below, serve to explain the principles of the present invention.

Turning to the figures, FIGS. 1 to 4 illustrate the basic concept and the function of the surgical stapling instrument according to the invention by means of an embodiment.

Figure 1:
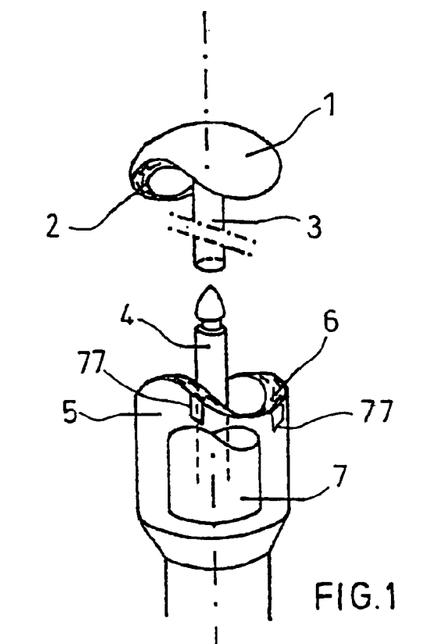
FIG. 1 is a schematic isometric view of the staple fastening assembly of a first embodiment of the surgical stapling instrument according to the invention, the anvil being removed from the cartridge device (open position)

As can be seen in FIG. 1, a wavy-shaped staple-forming face 2 (having an annular or circular cross section) of an anvil 1 and a wavy-shaped end face 6 of a cartridge device 5 (having an annular or circular cross section as well) can be fitted to each other. The connection of the anvil 1 and the cartridge device 5 is ensured by a shaft 3 rigidly fastened to the anvil 1 and a lowerable and raisable trocar 4 (which comprises a trocar shaft) accommodated in the center of the cartridge device 5. A knife 7 having a wavy-shaped cutting edge is positioned within the cartridge device 5. Moreover, two closed rows of staples, which follow the wavy-shaped end face 6 of the cartridge device 5, are indicated by short dashes.

Figure 3:
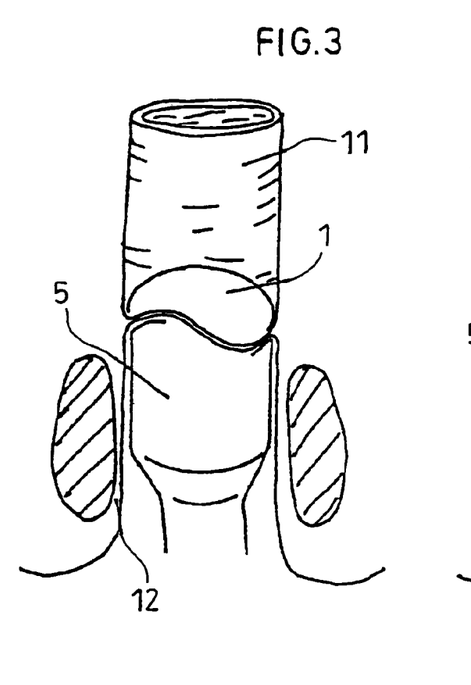
FIG. 3 is a schematic view of the instrument of FIG. 1 when it is inserted into the intestine (rectum) and the anvil is closed, a wavy-shaped intestinal seam being shown.

The stapling instrument of FIG. 1 is operated in the following way: In the usual manner, the anvil 1 is inserted into the oral end 11 of the intestine (rectum) of a patient, and the cartridge device 5 is inserted into the aboral end 12 of the intestine (rectum) (FIG. 3). The lumens or tissue portions destined to be joined in anastomosis can be tied to the anvil shaft and/or trocar shaft using a suture or other conventional tying technique. Following this, trocar 4 is attached to shaft 3 and then, by lowering trocar 4, the wavy-shaped staple-forming face 2 of anvil 1 and the wavy-shaped end face 6 of the cartridge device 5 are moved towards each other. After this, using the staples situated in the cartridge device 5, a wavy-shaped intestine seam is completed by "firing" the instrument.

Figure 4:
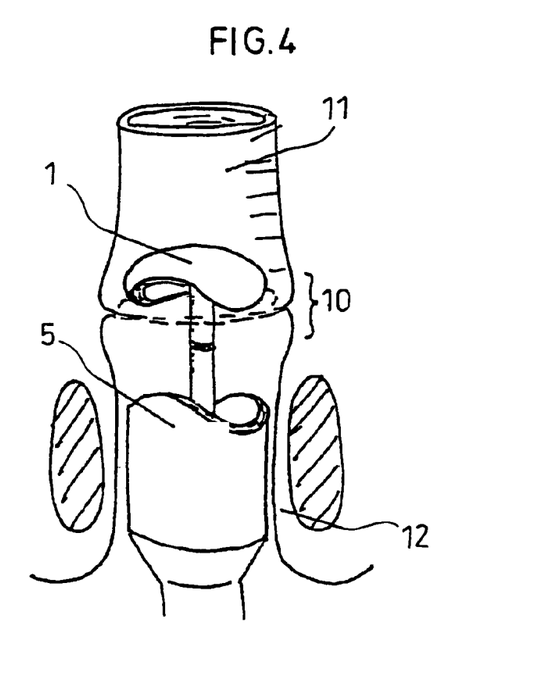
FIG. 4 is a view similar to FIG. 3, the intestinal seam being shown in a plane state, when it has a functionally longer perimeter, and the anvil being represented in an open position.

At the same time, the wavy-shaped knife 7, which has a circular cross section, cuts out the unnecessary intestine parts. By raising trocar 4, the instrument is opened and the anvil can be conveniently pulled through the intestine seam 10, which is able to functionally stretch to a longer perimeter (FIG. 4).

Figure 2:
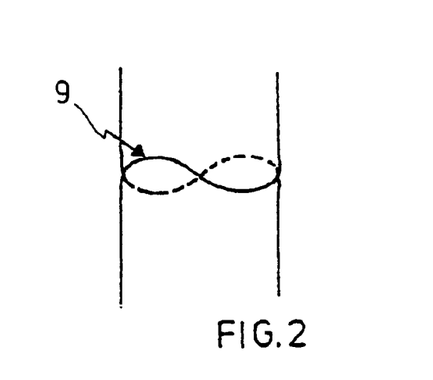
FIG. 2 is a isometric representation of the geometry of an annular intestine seam made by a surgical stapling instrument having a wavy-shaped staple line.

FIG. 2 schematically illustrates the wavy-shaped intestine seam 9 made by the stapling instrument of FIG. 1. Thanks to the particular shape of the staples and the configuration of the staple driving mechanism which will be described in detail below, the intestine seam 9 is less stiff than the stapled seams obtainable by prior art instruments, thereby allowing for a larger-diameter passageway, as shown in FIG. 4.

This facilitates the removal of the instrument and reduces the risk of developing seam insufficiency and stricture of the intestine seam.

Another embodiment of the surgical stapling instrument according to the invention is explained by means of FIGS. 5 to 13.

Figure 5:
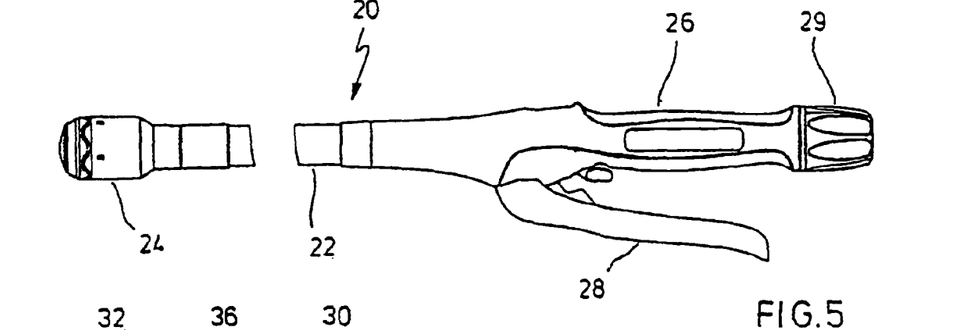
FIG. 5 is a side view of a second embodiment of the surgical stapling instrument according to the invention.

FIG. 5 is a side view of the complete surgical stapling instrument 20. The stapling instrument 20 comprises a frame having a body portion including a shaft 22 and a handle 26. A staple fastening assembly 24 is mounted at the distal end of the shaft 22. In the embodiment, the staple fastening assembly 24 can be removed from the shaft 22 and replaced by another one, if desired.

An actuator grip 28 is located in the proximal region of the stapling instrument 20. It can be swivelled towards handle 26 in order to "fire" the stapling instrument 20, i. e. for operating the staple driving device and the knife actuating device of the internal mechanism of the stapling instrument. A knob 29 can be rotated in order to axially shift a trocar shaft comparable to the trocar 4 of FIG. 1, in order to open or close the staple fastening assembly 24, i. e. in order to move the anvil of the stapling instrument 20.

Generally, the overall design and the mechanical components and drive mechanisms of the stapling instrument 20 are as in known stapling instruments (e.g. WO 01/54594); the three-dimensional arrangement and shape of the staples to form the staple lines and some details of the staple driving device, however, are different, as explained in the following.

Figure 6:
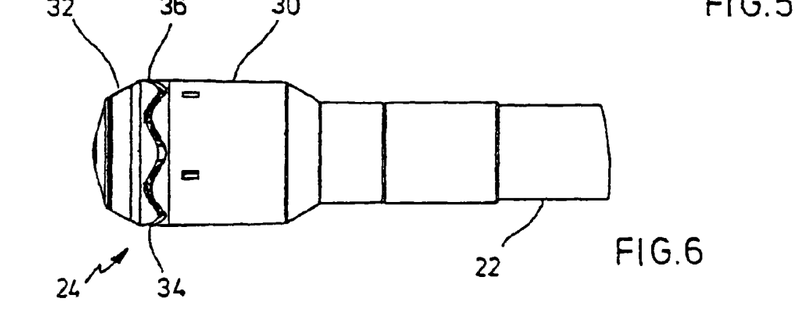
FIG. 6 is a magnified view of the distal end section of the stapling instrument of FIG. 5.

FIG. 6 is a magnified view of the staple fastening assembly 24 attached to the shaft 22. The staple fastening assembly 24 includes a cartridge device 30 and an anvil 32. The cartridge device 30 comprises a fixedly integrated cartridge or a removable and disposable cartridge containing two closed rows of staples. The end face 34 of the cartridge device has a wavy shape, as indicated in FIG. 6. Thus, the lines defining the closed rows of staples, which essentially follow the end face 34, have a wavy shape as well and are not confined to a plane perpendicular to the longitudinal axis of the staple fastening assembly 24, The anvil 32 has a staple-forming face 36 which is wavy-shaped as well and matches the wavy shape of the end face 34 of the cartridge device 30, see FIG. 6.

Figure 7:
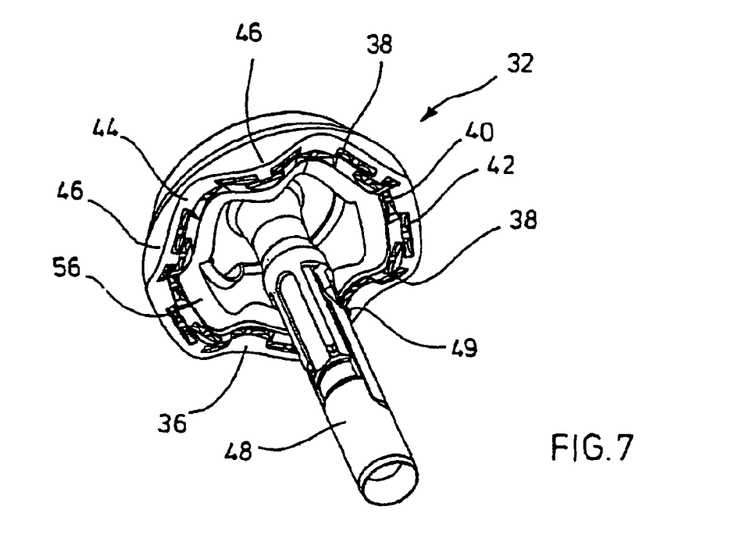
FIG. 7 is an isometric view of the staple-forming face of the anvil of the stapling instrument of FIG. 5.

FIG. 7 is an isometric representation of the staple-forming face 36 of anvil 32. The staple-forming face 36 comprises a plurality of staple-forming grooves 38, which are arranged in a first closed row 40 on the inner side and a second closed row 42 on the outer side. The staple-forming grooves 38 are arranged along the wavy shape, but remain perpendicular with respect to the staple driving direction. They also indicate the positions of the corresponding staples in the cartridge device 30, which are arranged in an inner first closed row and an outer second closed row, the individual staples of the rows being staggered to each other. In the embodiment, the wavy shape includes six full wavelengths with peaks at 44 and valleys at 46, see FIG. 7. Here, the designations "peak" and "valley" are relative to the wavy shape of the lines defining the closed rows of staples.

The anvil 32 comprises a hollow shaft 48 which can be attached to a trocar shaft extending along the longitudinal axis of the cartridge device 30, similar to the first embodiment shown in FIG. 1. A clip mechanism serves to lock the anvil shaft 48 at the trocar shaft.

Figure 8:
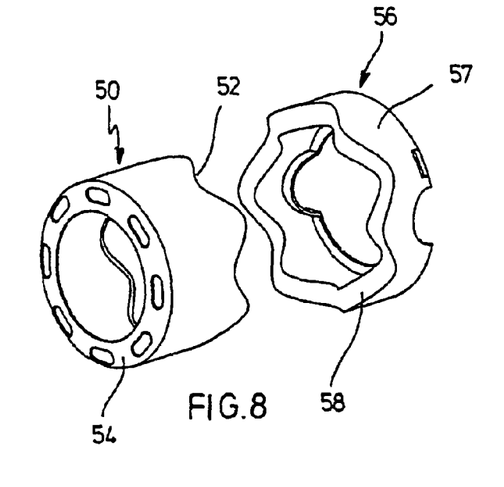
FIG. 8 is an isometric view of the circular knife and its counterpart of the stapling instrument of FIG. 5.
Figure 9:
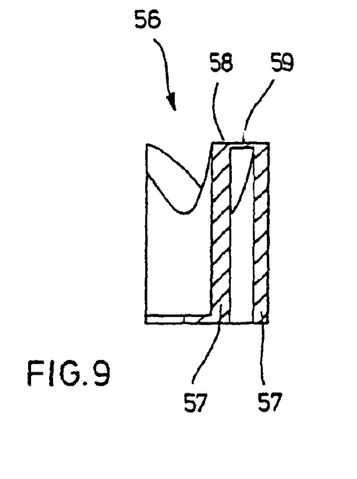
FIG. 9 is a partially sectional view of the counterpart shown in FIG. 8.

FIG. 8 illustrates a knife 50 having a closed and wavy-shaped cutting edge 52. By means of a mounting flange 54, the knife 50 is attached to a knife actuating device such that the knife 50 is contained within the cartridge device 30 on the inside of the inner closed row of staples. The peaks and valleys of the wavy shape of the cutting edge 52 are aligned to the peaks and valleys of the end face 34 of the cartridge device 30. Via the knife actuating device, the knife 50 can be moved towards the anvil 32, when the actuator grip 28 is operated, like in a conventional stapling instrument.

The anvil 32 includes a counter-part 56 which is aligned to the knife 50 when the anvil 32 is attached to the cartridge device 30, see FIGS. 7 and 8. The counterpart 56 is preferably made of a plastic material and comprises two side walls 57 and, at the wavy-shaped end face 58, a thin wall 59, see FIG. 9. During the initial instance of the cutting action, the wall 59 supports the tissue to be cut by the knife 50, and afterwards the cutting edge 52 penetrates the wall 59 which performs like a known cut washer.

Figure 10:
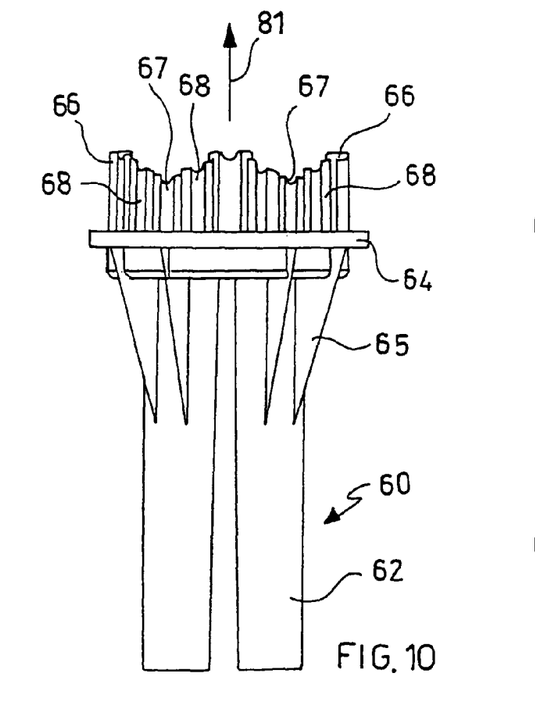
FIG. 10 is a side view of the distal part of the staple driving device of the stapling instrument of FIG. 5.

FIG. 10 is a side view of the distal section of the staple driving device 60 of the stapling instrument 20. When the actuator grip 28 is operated, the staple driving device 60 is moved in the direction of the arrow shown in FIG. 10, which causes the staples to penetrate the tissue clamped between the cartridge device 30 and the anvil 32. In contrast to the rather complex staple driving device of the prior art (e.g. WO 01/54594) all of the staples are driven in the same axial direction, i. e. in the direction of the arrow in FIG. 10. Thanks to the shape of the staples and the configuration of the staple pushers described below, the invention obviates the necessity to move the individual staples in a direction which is essentially perpendicular to the local surface of the end face 34 of the cartridge device 30, thereby consenting to simplify the staple driving device 60.

Figure 11:
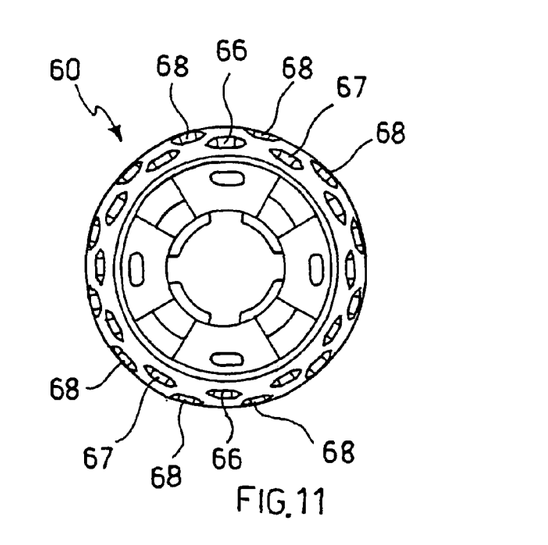
FIG. 11 is a top view of the staple driving device of FIG. 10.

In the staple driving device 60, an actuator shaft 62 guided inside shaft 22 supports a base plate 64 which is reinforced by ribs 65. As shown in FIGS. 10 and 11, two rows of pushers emerge from the base plate 64, i. e. a circular row of a total of twelve first pushers 66, 67 on the inside and a circular row of a total of twelve second pushers 68 on the outside. The first pushers include long ones 66 located at the positions of the peaks of the line defining the first closed row of staples and short ones 67 located at the positions of the valleys of this line, wherein each first pusher has a substantially straight push surface perpendicular to the axial staple driving direction. The second pushers 68 include a sloped push surface 70 which is inclined or slanting with respect to a plane perpendicular to the axial staple driving direction, see FIG. 10. Each of the second pushers 68 is arranged staggered and with circumferential overlap to respectively two adjacent first pushers 66, 67, see FIG. 11. Moreover the sloped push surface 70 of the second pushers 68 is substantially straight and extends in a direction parallel to the direction of the corresponding portion of the end face 58, 34 of the cartridge device, through which the staple is expellable by the staple driving device.

Figure 12:
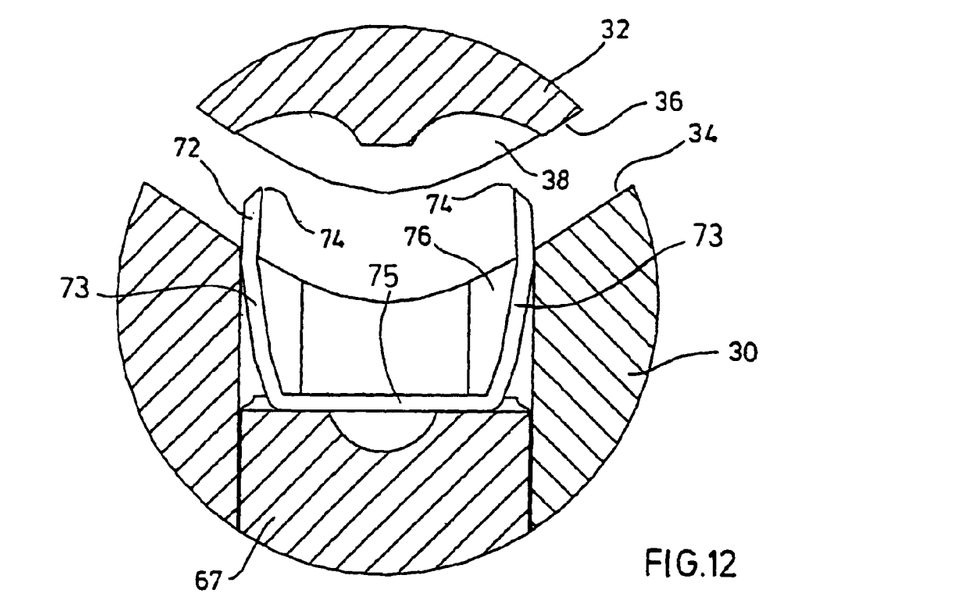
FIG. 12 and FIG. 13 are close-up views of details of the staple driving mechanism of the stapling instrument of FIG. 5.

FIG. 12 is a magnified longitudinal section which illustrates the operation of one of the first pushers, in this case of a first pusher 67 used to drive a staple 72 located at a valley of the line defining the first closed row of staples.

The staple 72 has a generally U-shaped symmetrical shape with two longitudinal legs 73 terminating in two pointed free ends 74 and a transverse basis 75 (the so called "crown") connecting the legs 73 on a side opposite the pointed free ends 74. Both legs 73 are approximately straight and extend substantially in the same longitudinal direction corresponding to the axial staple driving direction and the basis 75 is substantially straight and perpendicular to the longitudinal direction of the legs 73. Staple 72 is slidably housed inside a guide slot 76 defined in the cartridge device 30. The pointed ends 74 of the staple 72 are pointing towards the corresponding staple-forming groove 38 at the staple-forming face 36 of anvil 32. When the staple driving device 60 is advanced in distal direction, i. e. towards the anvil, the first pusher 67 moves in the axial staple driving direction and drives the staple 72, guided by the guide slot 76 through the tissue clamped between the end face 34 of the cartridge device 30 and the anvil 32, until the free ends 74 of the staple 72 are formed by means of the staple-forming groove 38.

A first pusher 66 located at a peak of the staple line works in the same, conventional manner. Since the staples 72 of the first closed row of staples are located at the peaks and valleys of the staple line, a conventional drive mechanism including an axial movement of the first pushers 66, 67 and a conventionally shaped surgical staple 72 achieves the desired effect of locally penetrating the tissue in a perpendicular manner and fastening a staple having a local "crown" length substantially equal to the corresponding local tissue length.

Figure 13:
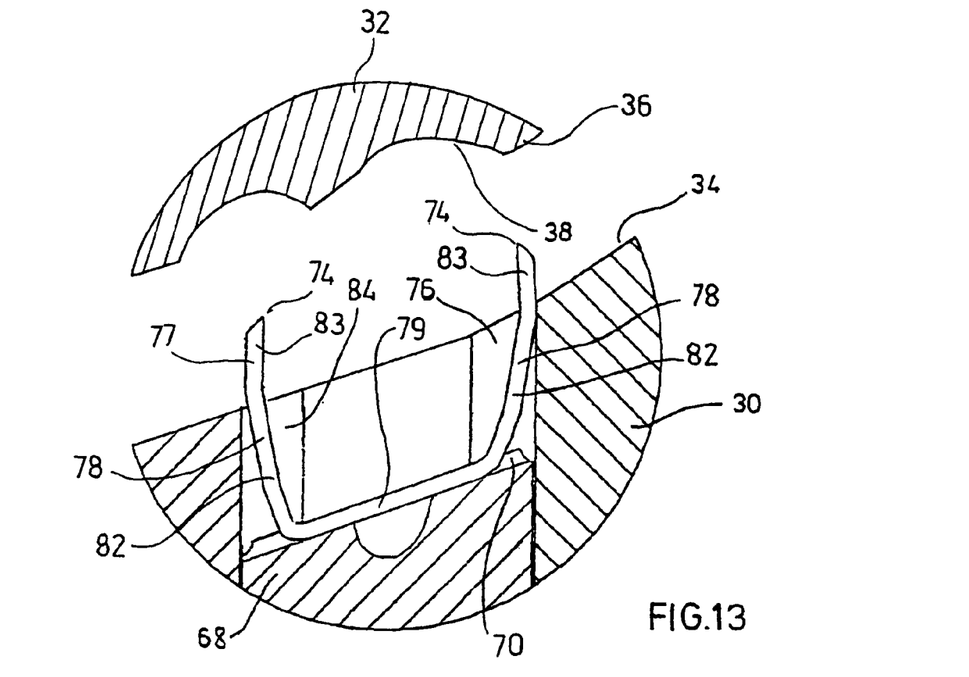

FIG. 13 illustrates the operation of a second pusher 68 which is configured to apply a staple 77 of the second closed row of staples by means of its sloped push surface 70.

The staple 77 is located in between a peak and a valley of the wavy staple line and will be expelled through a portion of the end face 34, 58 being non-orthogonal to the "firing"-direction of the stapling instrument, i.e. to its axial staple drive direction. Therefore, according to the invention, the staple 77 is given a substantially different shape compared with the staples known in the art. In particular, the staple 77 has a generally U-shaped non-symmetrical shape with two longitudinal legs 78 terminating in two pointed free ends 74 and a transverse basis 79 (the so called "crown") connecting the legs 78 on a side opposite the pointed free ends 74. Both legs 78 are preferably approximately straight and extend substantially in the same longitudinal direction corresponding to the axial staple driving direction and the basis 79 is preferably straight and inclined (i.e. oblique or slanted) to a plane 80 perpendicular to the longitudinal direction 81 of the legs 78. The angle of inclination α defined between the basis 79 and the plane 80 is advantageously comprised between 5° and 85°, preferably between 20° and 70°, and even more preferably between 30° and 60° and is selected such as to obtain at least an approximately parallel orientation of the staple basis 79 and the corresponding end face 34, 58 of the staple cartridge 30.

Preferably, the staple 77 extends completely within a single plane.

In accordance with an embodiment, the legs 78 of the staple 77 comprise an elongate base portion 82 and an elongate terminal portion 83. The base portions 82 slightly diverge from another while extending from the basis 79 towards the terminal portions 83 such as to define together with the basis 79 an irregular trapezium having its minor basis defined by the basis 79 and its two inclined sides defined by the base portions 82. The terminal portions 83 are preferably substantially parallel to each other or, alternatively, they slightly converge from the base portions 82 towards their pointed ends 74. Normally, the average or mean direction of the terminal portions 83 of both staple legs 78 will define the longitudinal direction 81 of the staple 77.

The staple 77 according to the invention is preferably made of a metallic material and fabricated by cutting of lengths from an endless metal wire and bending them in a single plane to the above described non-symmetrical shape.

Staple 77 is slidably housed inside a guide slot 84 defined in the cartridge device 30. The guide slot 84 extends in the very same axial staple driving direction as the above described guide slot 76. Advantageously, all guide slots 76, 84 are extending in the same direction. The pointed ends 74 of the staple 77 are pointing towards the corresponding staple-forming groove 38 at the staple-forming face 36 of anvil 32.

When the staple driving device 60 is advanced in distal direction, i. e. towards the anvil, the second pusher 67 moves in the axial staple driving direction and its sloped push surface 70 which has substantially the same orientation as the slanted staple basis 79 and which is in direct contact with said staple basis 79, drives the staple 77, guided by the guide slot 84 through the tissue clamped between the end face 34 of the cartridge device 30 and the anvil 32, until the free ends 74 of the staple 77 are formed by means of the staple-forming groove 38.

Figure 10A:
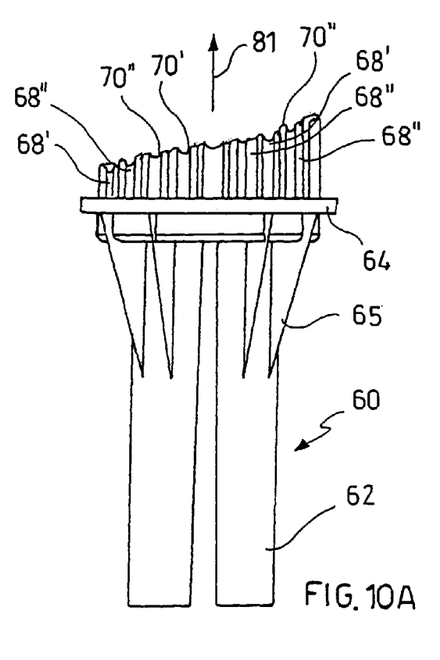
FIGS. 10A and 11A are side and top views, respectively, of the distal part of a staple driving device according to a further embodiment of the invention.
Figure 11A:
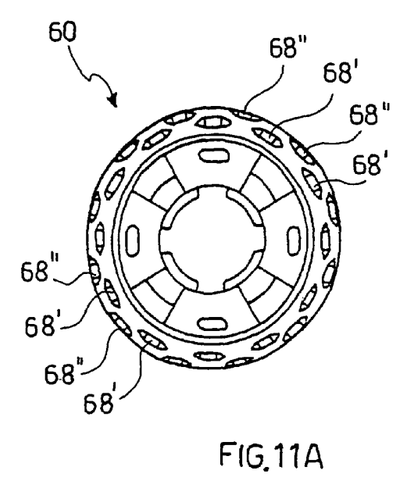

FIGS. 10A and 11A illustrate an alternative embodiment of a staple driving device with two rows of pushers 68', 68" including a sloped push surface 70', 70" which is inclined or slanting with respect to a plane perpendicular to the axial staple driving direction, see FIG. 10A. Each of the pushers 68' of the inner row is arranged staggered and with circumferential overlap to respectively two adjacent pushers 68" of the outer row, see FIG. 11A. The sloped push surface 70', 70" of the pushers 68', 68" is substantially straight and extends in a direction parallel to the direction of the corresponding portion of the end face 58, 34 of the cartridge device, through which the staple is expellable by the staple driving device. In this configuration almost all staples (except the staples defining the valley and peaks of the wave) can have a inclined basis, thereby simplifying the loading of the staples in the cartridge. The apexes of the wavy shape can be covered by traditional staples or by two staples with inversely inclined basis which slightly overlap in the region of the apex.

Thanks to the combination of an axial drive direction oblique to the end face 34, 58 of the cartridge device and a sloped push surface 70 parallel with a slanted staple basis 79 and with the corresponding (inclined) portion of the end face 34, 58, a conventional drive mechanism including an axial movement of the first pushers 66, 67 and second pushers 68 achieves the desired effect of locally penetrating the tissue and fastening a staple having a (sloping) local "crown" length substantially equal to the corresponding (sloping) local tissue length. In this case, the penetration direction is not any more perpendicular but somewhat oblique to the tissue plane, consenting a better flattening of the oblique portions of the resulting wavy stapled seam without substantially tensioning the tissue.

FIGS. 16, 17, 18 and 19 show in more detail the principle relationships between the staple shape, the orientation of the staple with respect to the wavy end face of the staple fastening device, the orientation of the sloped push surface of the pusher and the staple drive direction according to the invention.

Figure 14:
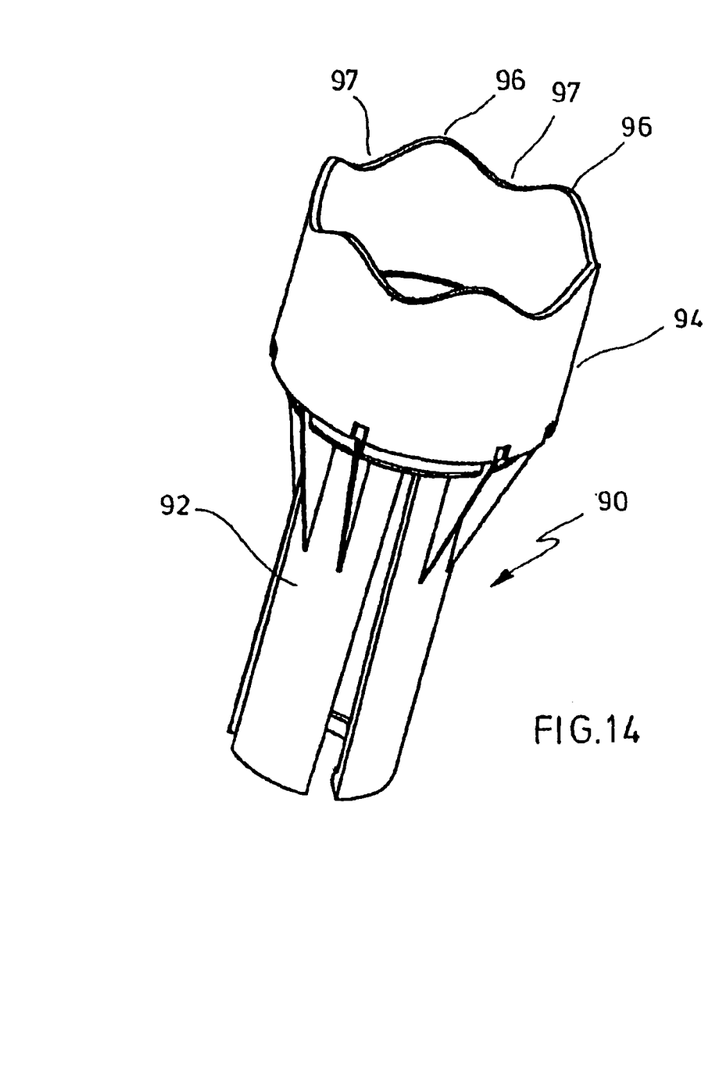
FIG. 14 is an isometric view of the end section of the staple driving device of another embodiment of the surgical stapling instrument according to the invention.
Figure 15:
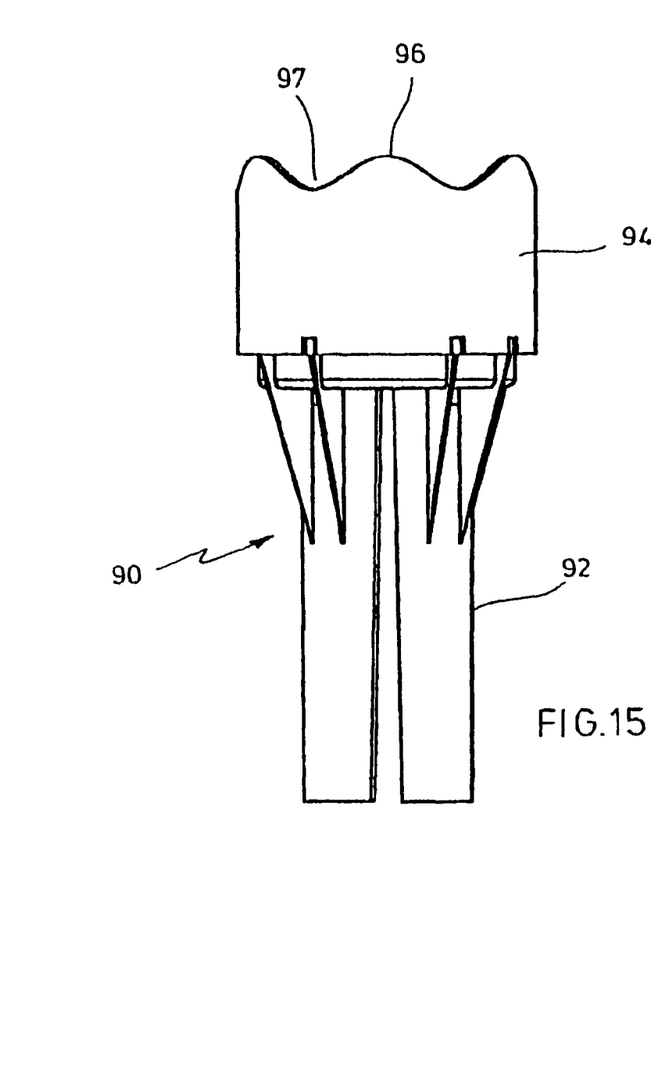
FIG. 15 is a side view of the end section of the staple driving device of FIG. 14.
Figure 16:
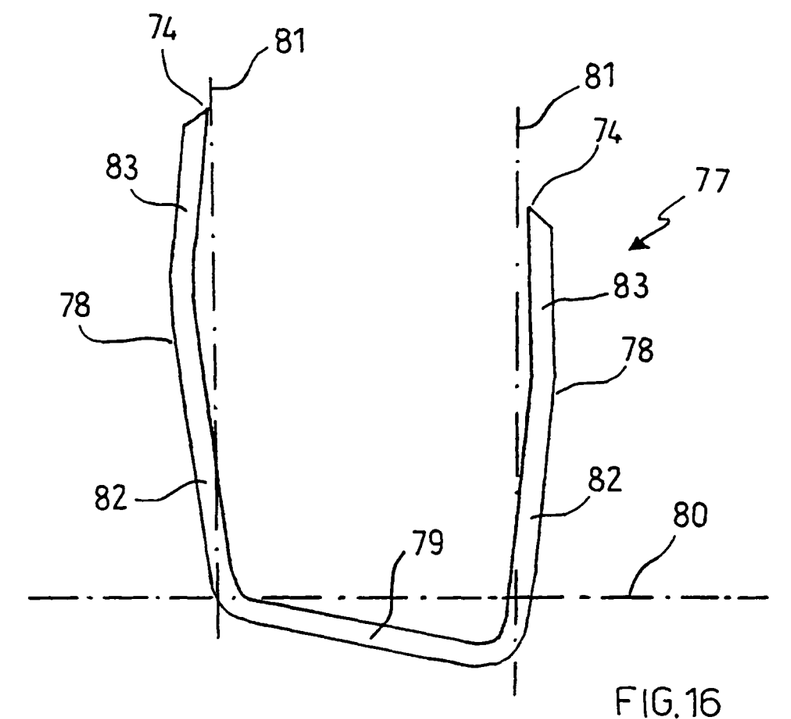
FIG. 16 is a side view of a staple according to the invention for use in the surgical stapling instruments according to the invention.
Figure 17:
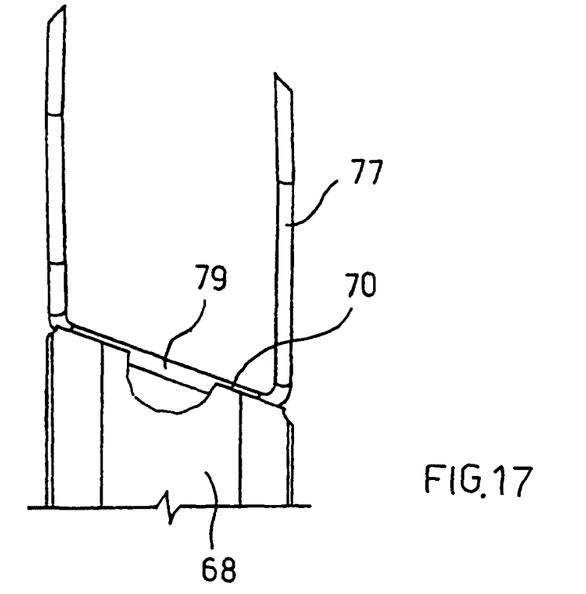
FIG. 17 is a side view of a detail of a staple drive mechanism carrying the staple shown in FIG. 16.
Figure 18:
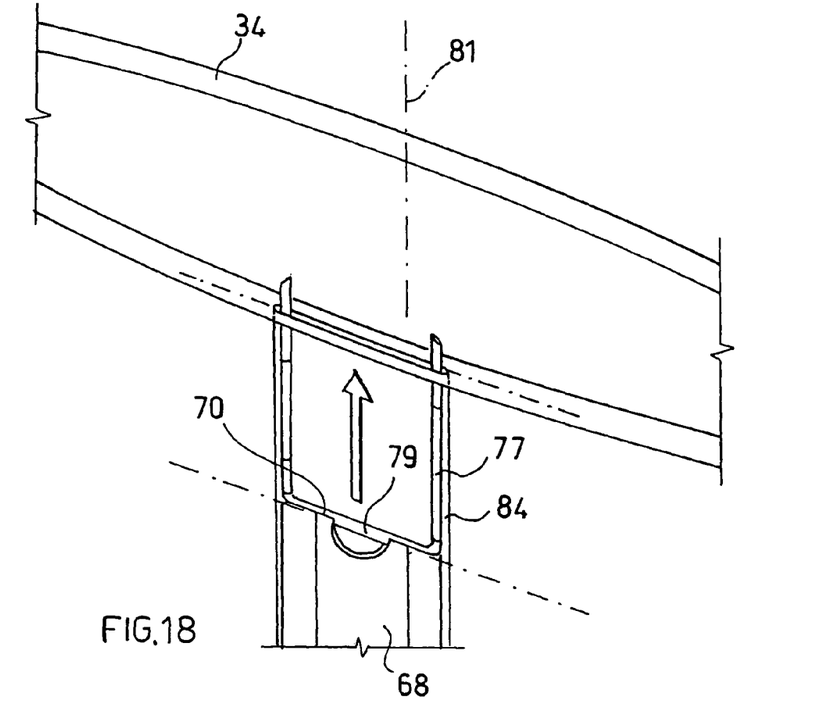
FIG. 18 is an isometric transparent view of a detail of a staple cartridge device according to an embodiment of the invention for use in a surgical stapling device according to the invention.
Figure 19:
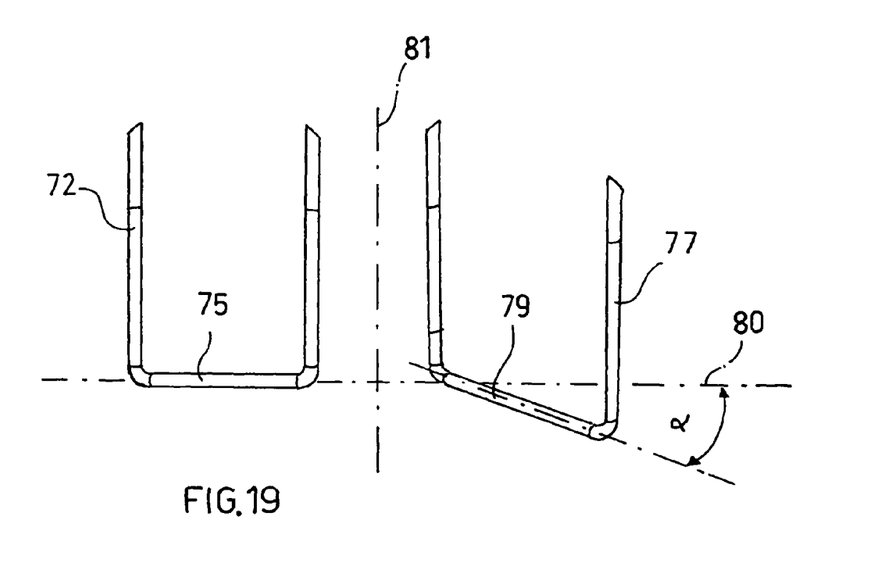
FIG. 19 is a side view of a symmetrical staple known in the art and an non-symmetrical staple according to the invention.

FIGS. 14 and 15 show another embodiment of the distal part 90 of the staple driving device. In this case, an actuator shaft 92 supports a sleeve structure 94 having a wavy-shaped end with peaks 96 and valleys 97. The sloped areas in between the peaks 96 and the valleys 97 act similar to the sloped push surfaces 70 of the embodiment of FIGS. 10 and 11 and are adapted to directly contact and engage the inclined staple basis 79 of staples 77, without the interposition of any intermediate parts, as occurs in the prior art devices.

Figure 23:
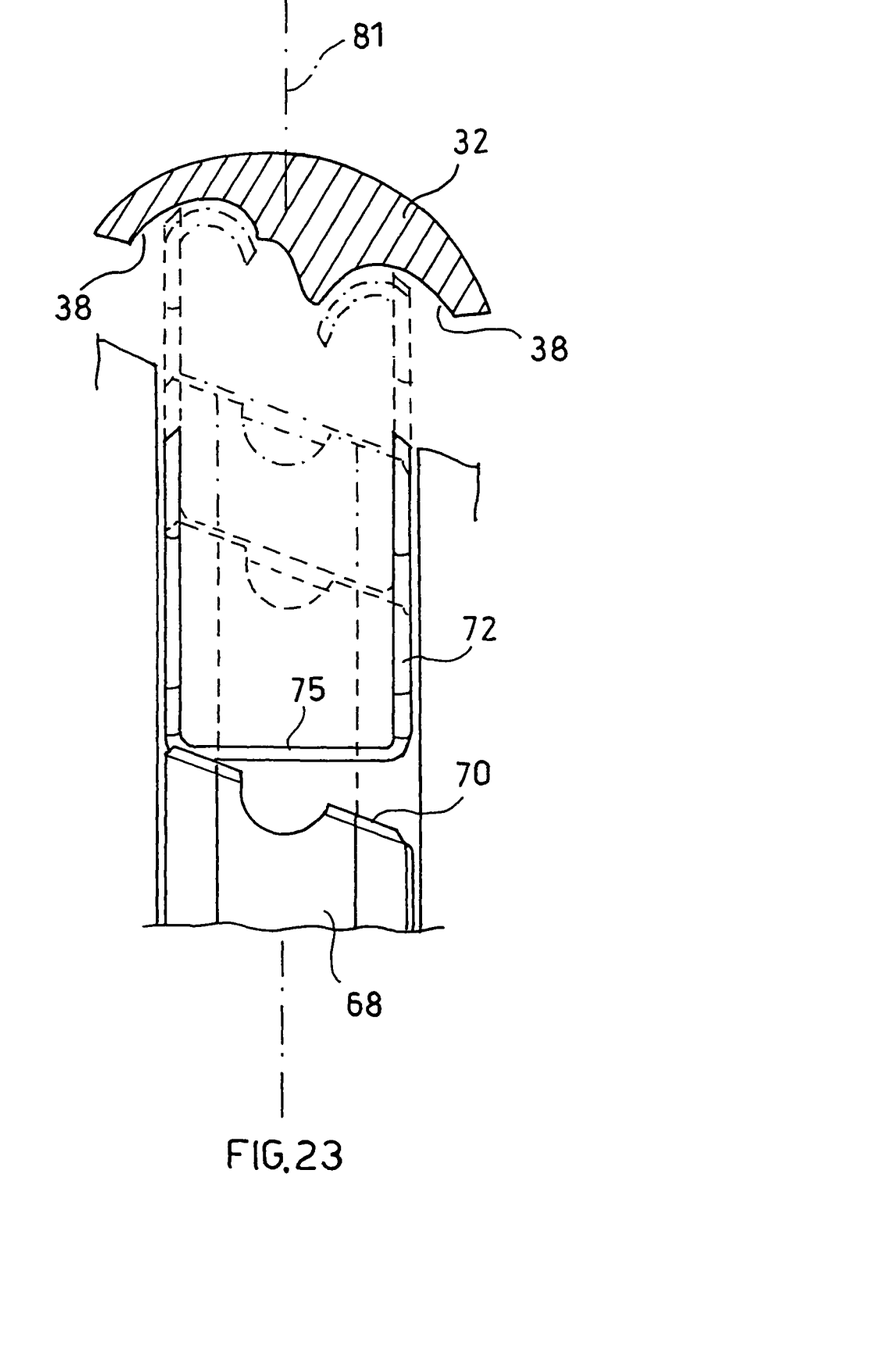
FIG. 23 is a schematic representation of a further use of the surgical stapling instrument according to the invention.

FIG. 23 shows a different way of using the surgical stapling instrument according to the present invention, in which the surgical instrument is employed in connection with traditional staples, i.e. with the staples having a basis substantially perpendicular to the legs. Thanks to the inclined push surface 70 of the pushers and the axially offset arrangement of the staple forming grooves at the anvil staple forming surface, during operation of the stapler, the traditional staple will be firstly deformed to a shape in which the basis is slanted with respect to the legs (dashed line) and afterwards the pointed free ends will be clinched inwardly (chain dotted line), thereby fastening the staple to the tissue.

When the surgical stapling instrument 20 is used, its shaft 22 and the staple fastening assembly 24 are introduced into the hollow organ where the anastomosis is to be performed. Generally, the end region of one part of the organ is placed over the end face 34 of the cartridge device 30, whereas the end region of the other part is placed over the anvil 32 such that the anvil shaft 48 protrudes and connects or can serve to connect the anvil 32 to the cartridge device 30. By means of the moving device mentioned above, which is operated via the knob 29, the anvil 32 is moved relative to the cartridge device 30 until the remaining gap between the anvil 32 and the cartridge 30 device is essentially filled by the tissue of both parts of the hollow organ. In a preferred embodiment of the surgical stapling instrument, it is possible to adjust the size of this gap in a well-defined manner. Thereafter, the staple driving device 60 is actuated by means of the actuator grip 28 in order to drive the staples out of the cartridge device 30 towards the anvil 32. The pointed ends of the staples penetrate the tissue in-between and are bent by the anvil 32 so that the staples are closed. Afterwards, the knife actuating device moves the knife 50 towards the anvil 32 so that the cutting edge 52 of the knife 50 penetrates the tissue. The knife actuating device is preferably coupled to the staple driving device so that only actuator grip 28 has to be operated in order to perform the functions of stapling and cutting the tissue almost simultaneously. The presence of two closed rows of staples, which are staggered with respect to each other, ensures a reliable connection of both parts of the hollow organ.

At the end of the procedure, the surgical stapling instrument 20 can be retracted after the gap between the cartridge device 30 and the anvil 32 has been increased in order to release the clamped and stapled tissue edge. The shape of the closed rows of staples provides a relatively large overall length of the staple lines, so that the tissue at the anastomotic site can yield and the anvil 32 can be easily moved through the opening created by the cutting edge 52 of the knife 50. The excised tissue portion remains in the surgical stapling instrument 20.

Although an embodiment of a circular surgical stapling instrument has been described in detail, it is not the intention of the applicant to limit the scope of the claims to such particular stapling instrument. The staple 77 according to the invention can be advantageously used in different staple cartridge devices and different surgical staplers having tissue interfaces which are at least partially inclined with respect to the staple driving direction.

Figure 20:
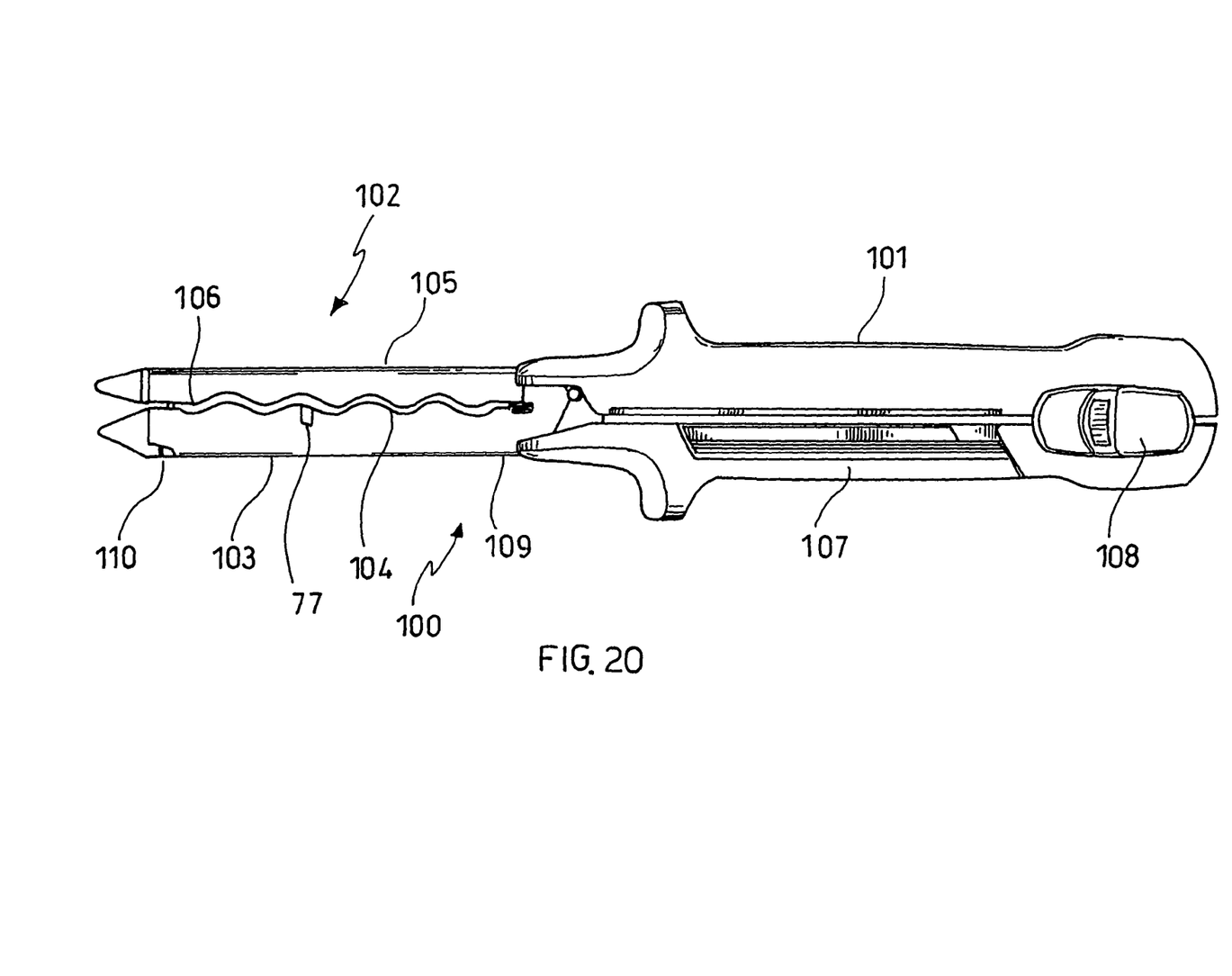
FIGS. 20 to 22 are schematic side views of further surgical stapling instruments with linear stapling features suitable for the use of the staple and staple cartridge device according to the invention.
Figures 21, 22:
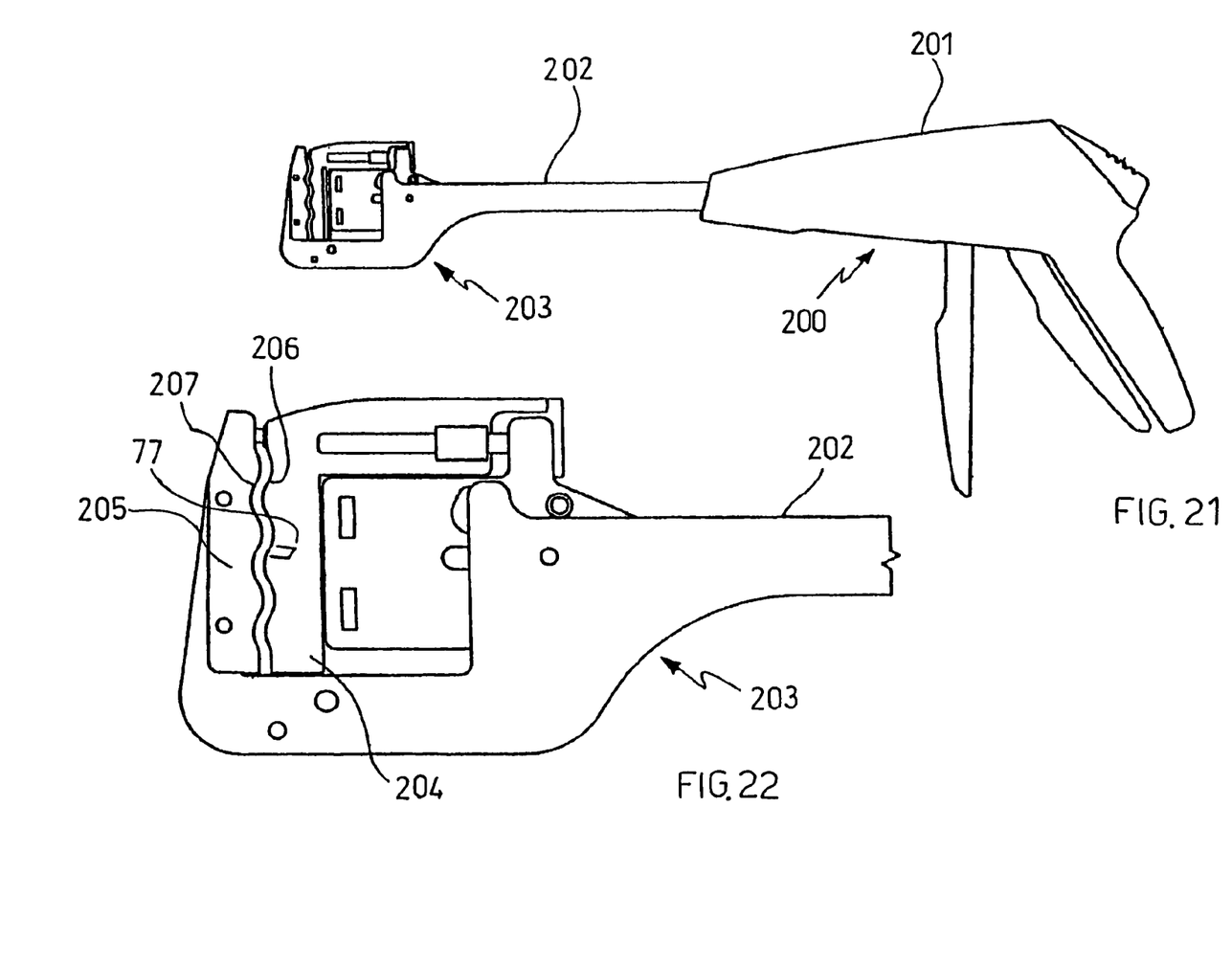

FIGS. 20 to 22 show examples of surgical stapling instruments having a substantially linear open stapling jaw with wavy tissue interfaces and staple driving devices and staples which are shaped, arranged and movable with respect to the wavy tissue interfaces in the same way as has been described in relation with the embodiment of FIGS. 12, 13, 16, 17, 18 and 19.

The instrument 100, illustrated in FIG. 20, comprises a body portion 101 with integrated handle and a jaw assembly (i.e. staple fastening assembly) 102. The jaw assembly 102 includes a cartridge device 103, which comprises a first wavy tissue interface 104, and an anvil 105, which comprises a second wavy tissue interface 106. In the embodiment, the cartridge device 103 contains e.g. four parallel straight rows of staples (few staples 77 have been schematically indicated in the figure) of the kind described above and a knife running along the center line of the staple arrangement for sequentially cutting tissue gripped between the cartridge device 103 and the anvil 105.

To operate the instrument 100, the anvil 105 is moved towards the cartridge device 103 in a parallel relationship by means of a lever 107 in order to grip or clamp tissue between the cartridge device 103 and the anvil 105. In the state shown in FIG. 3, the lever 107 is swivelled in a position parallel to the body portion 101. Then an actuator 108 is pushed along the body portion 101 in distal direction, which causes the staples to be expelled from the cartridge device 103 for penetrating the tissue, the pointed ends of the staples being bent by the anvil 105, and to move the knife from the proximal end region 109 to the distal end region 110 of the cartridge device 103 for sequentially cutting the tissue.

FIG. 21 shows yet another surgical instrument, denoted by reference numeral 200, suitable to use the staples and staple cartridge devices according to the invention. The instrument 200 includes a handle portion 201, a shaft 202 and a jaw assembly (i.e. staple fastening assembly) 203 at the distal end of the shaft 202. FIG. 22 shows the jaw assembly 203 with its cartridge device 204 and an anvil 205. Whereas in the instrument 100 the respective cartridge device and anvil are aligned in parallel to the longitudinal axis of the instrument, the anvil 205 and the cartridge device 204 extend transversally with respect to the shaft 202, as in the first embodiment of the anastomotic stapling instrument. The instrument 200 is designed for open surgery. The anvil 205 is rigidly connected to an extension of shaft 202, and the cartridge device 204 can be moved towards and away from the anvil 205, while a parallel relationship between a first wavy tissue interface 206 provided at the cartridge device 204 and a second wavy tissue interface 207 provided at the anvil 205 is maintained. The staple shape and arrangement as well as the staple driving device is analogous to those described in relation with the other embodiments. A few staples 77 and their position in the cartridge device have been schematically indicated in FIG. 22.

The invention claimed is:

1. A surgical stapling instrument comprising:
a frame having a body portion (22) and a handle (26),
a staple fastening assembly (1, 5; 24) in the distal region of said instrument, the staple fastening assembly (1, 5; 24) including a cartridge device (5; 30) which comprises at least one row of staples (72, 77) and a generally wavy first tissue interface (34), and an anvil (1; 32) which is movable relative to the cartridge device (5; 30) and having a generally wavy second tissue interface (36) adapted to cooperate with the first tissue interface (34) of the cartridge device (5; 30) for clamping tissue therebetween and forming the ends (74) of the staples (72, 77) exiting from the cartridge device (5; 30),
a moving device adapted to move the anvil (1; 32) relative to the cartridge device (5; 30),
a staple driving device (60; 90) adapted to drive all the staples (72, 77) in a same staple driving direction out of the cartridge device (5; 30) towards the anvil (1; 32), wherein the staples comprise non-symmetrical U-shaped staples (77) having two legs (78) with free pointed ends (74) extending in a longitudinal direction (81) and facing toward the anvil (1; 32) and a transverse basis (79) connecting the legs (78), wherein said basis (79) is inclined with respect to the longitudinal direction (81), such that the basis (79) has a length greater than an orthogonal projection of the basis on a plane (80) perpendicular to the longitudinal direction (81) of the legs (78),
wherein said non-symmetrical staples are arranged in the cartridge device such that:
the longitudinal direction of the legs of the non-symmetrical staples is parallel to the staple driving direction, and the inclined basis of each of said non-symmetrical staples is substantially parallel to a corresponding portion of the first tissue interface through which the non-symmetrical staple is expellable by the staple driving device, said portion of the first tissue interface being non-orthogonal to said staple driving direction.

2. A surgical stapling instrument according to claim 1, wherein the staple driving device (60; 90) comprise pushers (68) having a sloped push surface (70) directly abutting against the basis (79) of said non-symmetrical staple (77), wherein said push surface (70) is inclined with respect to a plane (80) perpendicular to the staple driving direction (81) and parallel to the corresponding portion of the first tissue interface, through which the non-symmetrical staple is expellable by the staple driving device said portion of the first tissue interface being non-orthogonal to said staple driving direction.

3. A surgical stapling instrument according to claim 1, wherein the sloped basis (79) of the staple (77) is substantially straight and defines with said plane (80) perpendicular to the longitudinal direction (81) of the legs (78) an angle (α) comprised between 20° and 60°.

4. A surgical stapling instrument according to claim 3, wherein the staple (77) extends completely within a single plane.

5. A surgical stapling instrument according to claim 4, wherein the legs (78) of the staple (77) comprise an elongate base portion (82) and an elongate terminal portion (83), in which:
- said base portions (82) slightly diverge from another while extending from the basis (79) towards the terminal portions (83);
- said terminal portions (83) are substantially parallel to each other.

6. A surgical stapling instrument according to claim 1, wherein the cartridge device (30) defines a plurality of guide slots (84) which slidably house said staples (77; 72) and opening out in the first tissue interface, in which all guide slots (84, 76) of the cartridge device (30) are parallel to the same staple driving direction (81).

7. A surgical stapling instrument comprising:
a frame having a body portion (22) and a handle (26),
a staple fastening assembly (1, 5; 24) in the distal region of said instrument, the staple fastening assembly (1, 5; 24) including a cartridge device (5; 30) which comprises at least one row of staples (72, 77) and a generally wavy first tissue interface (34), and an anvil (1; 32) which is movable relative to the cartridge device (5; 30) and having a generally wavy second tissue interface (36) adapted to cooperate with the first tissue interface (34) of the cartridge device (5; 30) for clamping tissue therebetween and forming the ends (74) of the staples (72, 77) exiting from the cartridge device (5; 30),
a moving device adapted to move the anvil (1; 32) relative to the cartridge device (5; 30),
a staple driving device (60; 90) adapted to drive all the staples (72, 77) in a same staple driving direction out of the cartridge device (5; 30) towards the anvil (1; 32),
wherein the staple driving device (60; 90) comprises pushers (68) having a sloped push surface (70) directly abutting against the basis of an initially symmetrical U-shaped staple, wherein said push surface (70) is inclined with respect to a plane (80) perpendicular to the staple driving direction (81) and parallel to a corresponding portion of the first tissue interface, through which the initially symmetrical staple is expellable by the staple driving device, said portion of the first tissue interface being non-orthogonal to said staple driving direction,
wherein staple forming grooves at the anvil staple forming surface are offset in the staple driving direction, such that during operation of the stapling instrument, the initially symmetrical U-shaped staple will be firstly pre-deformed by the inclined push surface and the offset staple forming grooves to a non-symmetrical U-shape having two legs with free pointed ends extending in said staple driving direction and facing toward the anvil and a transverse basis connecting the legs, wherein said basis is inclined with respect to the staple driving direction, and afterwards the pointed free ends of the pre-deformed non-symmetrical U-shaped staple will be formed to fasten the staple to the tissue.

* * * * *